United States Patent [19]

Leupold et al.

[11] Patent Number: 4,977,283

[45] Date of Patent: Dec. 11, 1990

[54] PROCESS FOR THE OXIDATION OF 5-HYDROXYMETHYLFURFURAL

[75] Inventors: Ernst I. Leupold, Neu-Anspach; Matthias Wiesner, Mainz; Merten Schlingmann, Königstein; Knut Rapp, Offstein, all of Fed. Rep. of Germany

[73] Assignee: Hoechst Aktiengesellschaft, Frankfurt am Main, Fed. Rep. of Germany

[21] Appl. No.: 387,086

[22] Filed: Jul. 27, 1989

[30] Foreign Application Priority Data

Jul. 30, 1988 [DE] Fed. Rep. of Germany ....... 3826073

[51] Int. Cl.[5] .................. C07D 307/48; C07D 307/68
[52] U.S. Cl. .................................... 549/484; 549/485; 549/488

[58] Field of Search ........................ 549/484, 485, 488

[56] References Cited

U.S. PATENT DOCUMENTS 3,326,944  6/1967  Lew .................................... 549/485

OTHER PUBLICATIONS

J. J. Blanksma, *Chemisches Zentralblatt:*(1910)T, 539.
S. Morikawa, Chem. Abstr. 92:198181a, (1980).

*Primary Examiner*—Howard L. Raymond

[57] ABSTRACT

A process for the oxidation of 5-hydroxymethylfurfural which comprises oxidizing 5-hydroxymethylfurfural in an aqueous medium with oxygen in the presence of a catalyst which contains at least one metal of the platinum group.

23 Claims, No Drawings

PROCESS FOR THE OXIDATION OF 5-HYDROXYMETHYLFURFURAL

DESCRIPTION

The present invention relates to the catalytic oxidation of 5-hydroxymethylfurfural to form products which can be put to a multiplicity of uses and which in particular can be used as intermediates for the preparation of surfactants, plastics and resins.

It is known to oxidise 5-hydroxymethylfurfural without the co-use of catalysts, using various oxidizing agents, such as concentrated nitric acid (J. J. Blanksma, Chemisches Zentralblatt 1910 I, 539) or a mixture of dimethyl sulfoxide on the one hand and acetic anhydride, dinitrogen tetroxide or nitric acid on the other hand (Morikawa, Chem. Abstr. Vol. 92 (1980), 198181a).

Essentially, three reaction products are found on the oxidation:

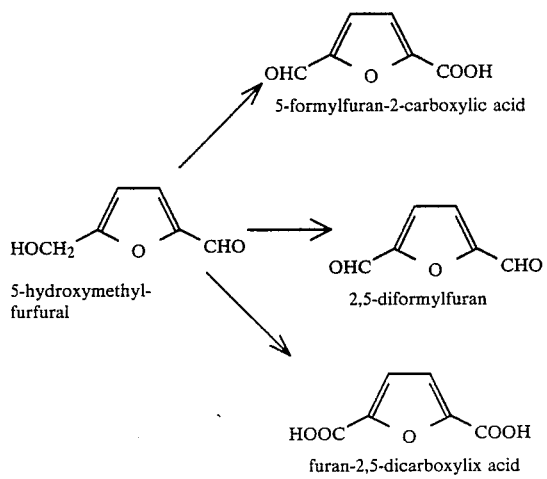

However, the methods hitherto known for the preparation of oxidation products of 5-hydroxymethylfurfural are associated with considerable disadvantages. When using the conventional reagents nitric acid, dinitrogen tetroxide and dimethyl sulfoxide, large amounts of undesired products, such as nitrous gases or sulfur compounds, depending on the particular reagents, inevitably form the disposal of which requires considerable expenditure. Likewise, it is very expensive to separate off excess oxidizing agent during working-up. There is thus a need for a process for the oxidation of 5-hydroxymethylfurfural which can be carried out without the said disadvantages in a technically simple manner.

The invention relates to a process for the oxidation of 5-hydroxymethylfurfural, which comprises oxidizing 5-hydroxymethylfurfural in an aqueous medium using oxygen as the oxidizing agent in the presence of a catalyst which contains at least one metal from the platinum group.

Suitable catalysts are those which contain metals of the platinum group, such as iridium, rhodium, ruthenium, but advantageously palladium and/or platinum. Catalysts which contain only platinum as the metal from the platinum group are very particularly preferred. The metals of the platinum group are preferably used on a support, particularly on activated charcoal. The metal, particularly platinum, content of the catalyst is preferably 1 to 10 by weight. Examples of suitable catalysts are commercially available catalysts having 5 to 10% by weight of platinum on activated charcoal.

The concentration of 5-hydroxymethylfurfural in the aqueous medium may vary within wide limits. It is preferably used in an amount from 5 to 30, particularly 10 to 20% by weight relative to the amount of water and solubilizer.

In order to avoid the precipitation of reaction products during the oxidation, it has proved advantageous, particularly at relatively high concentrations, to use a solubilizer which is inert toward the reactants under the reaction conditions, preferably in a concentration of 10 to 75% by weight, particularly 30 to 50% by weight, relative to the amount of water and solubilizer. Solubilizers used are expediently those which have relatively low volatility when oxygen is passed through the aqueous solution, so that a risk of explosion in the vapor space is substantially avoided; on the other hand, those solubilizers which are easily separated off, for example by distillation, after the oxidation are preferred.

Examples of suitable solubilizers are glycol ethers without free OH groups, such as glycol ethers of the formula $R^1O[CH_2CH(CH_3)O]_nR^2$, in which n is an integer from 1 to 4 and $R^1$ and $R^2$ in each case independently of one another denote $C_1$–$C_4$-alkyl. The dimethyl, diethyl or methyl ethyl ethers and the corresponding propylene glycol ethers of the said general formula with boiling points in the range from 100° to about 250° C., for example triethylene glycol dimethyl ether and particularly diethylene glycol dimethyl ether, are particularly suitable. Other ethers also, such as crown ethers, are suitable as solubilizers, it being necessary in each individual case to take particular account in the economics of the process of the expenditure for the separation and the costs of using the solubilizer.

Pure oxygen is the preferred oxidizing agent. However, it is also possible to use mixtures of oxygen with gases which are inert under the reaction conditions, for example in the form of air, for example mixtures of oxygen with inert gases or with air.

Generally, the operation is carried out at a total pressure of between 0.5 and 100 bar. The reaction velocity increases significantly with increasing partial pressure of oxygen; however, with regard to the economics of the process, the advantage of the higher reaction velocity may be over compensated by the higher expenditure on apparatus required due to the application of a higher pressure. A pressure range from atmospheric pressure up to 10 bar (absolute) is preferred, operation at atmospheric pressure being particularly simple to carry out.

As a rule, the process according to the invention is carried out at a temperature from 30° C. up to the boiling point of the aqueous medium, preferably from 50° to 95° C., particularly 60° to 90° C.

The reaction can be carried out in various ways with respect to the pH value, and the pH control may have an influence on the proportions of the individual products in the end product. Thus, for example, the reaction may be carried out in a medium which becomes acid due to the reaction products, i.e. in a pH range of below pH 7. Likewise, it is possible to control the pH value during the oxidation by the addition of bases, acids or buffer mixtures, a pH value of less than 8 as a rule being maintained. The oxidation may, however, also still be carried out at higher pH values.

It is possible, for example, by continuous addition of a base such as sodium hydroxide, potassium hydroxide or corresponding aqueous solutions of these bases, to establish a substantially constant pH value in the range from 6.5 to 8, preferably 7 to 7.5. In the latter mode of operation, the oxidation product furan-2,5-dicarboxylic acid is preferentially formed in the form of the di-salt. According to another embodiment, the oxidation is started at about pH 7 and continued without the addition of acids or bases. In the acid medium, 2,5-diformylfuran and 5-formylfuran-2-carboxylic acid preferentially form.

The process according to the invention takes place in a three-phase system comprising solid catalyst, aqueous medium and gaseous oxygen. It may be carried out in all apparatuses which are suitable for carrying out reactions in the liquid phase with or without the application of excess pressure. Examples of this are operating in a stirred vessel or in a bubble column with suspended catalyst. However, the oxidation may also be carried out as a fixed-bed reaction with a granular catalyst in a trickle-bed reactor.

The reaction time required for the formation of the desired reaction product in each case is expediently determined by withdrawing samples of the reaction solution at certain time intervals and analyzing them. For example, the yield of the reaction products can continually determined in a simple manner by analysis of a sample with the aid of high pressure liquid chromatography in comparison with standard solutions. It is advisable to optimize the reaction time, since if the passage of oxygen is unnecessarily prolonged this can lead increasingly to excessive oxidations, followed for example by decarboxylations, and thus to a loss in yield of the desired reaction products.

The reaction mixture can be worked up by known methods. In a suitable process, the solubilizer and the water are first removed by distillation and a subsequent purification by crystallization or extraction is carried out.

Compared with the conventional oxidation processes mentioned initially, the process according to the invention has the advantage that the formation of undesired products, such as nitrous gases or sulfur compounds, is avoided and the separation of excess oxidizing agent is also eliminated. In the catalytic oxidation according to the invention, apart from the desired products, only water is inevitably produced, which in any case is used as the solvent.

The oxidation products of 5-hydroxymethylfurfural are valuable intermediates for the preparation of plastics, surfactants and resins. For example, furan-2,5-dicarboxylic acid can be used as a component of polyesters, and the aldehydes 2,5-diformylfuran and 5-formylfuran-2-carboxylic acid can be used after reaction with long chain amines as surfactants, or in polymerization and copolymerization reactions for the preparation of novel plastics and resins.

EXAMPLES (1) 80 liters (STP) per hour of oxygen are introduced at a temperature of 70° C. from below through a glass frit into an externally heated, vertically arranged glass tube (diameter: 50 mm, length: 1200 mm), which is filled with a mixture of 162 g of 5-hydroxymethylfurfural, 1460 g of water and 81 g of a commercially available catalyst (5% by weight of platinum on activated charcoal). The pH value is kept at 7 to 7.5 by the continuous addition of 30% aqueous sodium hydroxide solution. After a reaction time of 2.5 hours the reaction solution contains 234 g of furan-2,5-dicarboxylic acid in the form of the disodium salt, corresponding to a yield of 91% of theory.

(2) In the apparatus described in Example 1, 1500 g of a 20% aqueous solution of 5-hydroxymethylfurfural are oxidized in the presence of 50 g of the catalyst used in Example 1 at a temperature of 85° C. with 80 (STP) liters per hour of oxygen. After a reaction time of 11 hours, during which the pH value was maintained at 7 to 7.5 by the addition of 30% aqueous sodium hydroxide solution, the reaction mixture contains 376 g of furan-2,5-dicarboxylic acid in the form of the disodium salt, corresponding to a yield of 79% of theory.

(3) In the apparatus described in Example 1, a mixture of 180 g of 5-hydroxymethylfurfural, 700 g of water, 700 g of diethylene glycol dimethyl ether and 75 g of a commercially available catalyst (5% by weight of platinum on activated charcoal) is reacted with oxygen at a temperature of 60° C. In contrast to Examples 1 and 2, no sodium hydroxide is added, so that the pH value falls, due to the formation of carboxyl groups, from an initial value of about 7 to below 7. After a reaction time of 8 hours the reaction mixture contains 122 g (61% of theory) of 5-formylfuran-2-carboxylic acid, 43 g (24% of theory) of 2,5-diformylfuran and 18 g (8% of theory) of furan-2,5dicarboxylic acid.

(4) The reaction described in Example 1 is carried out for 4 hours at 60° C. under otherwise identical conditions. The reaction solution contains 252 g of furan-2,5-dicarboxylic acid in the form of the disodium salt, corresponding to a yield of 98% of theory.

We claim:

1. A process for the oxidation of 5-hydroxymethylfurfural which comprises oxidizing 5-hydroxymethylfurfural in an aqueous medium at a pH value of at most 8 with oxygen in the presence of a catalyst which contains at least one metal of the platinum group.

2. A process as claimed in claim 1, wherein the platinum metal is palladium, platinum or a combination of palladium and platinum.

3. A process as claimed in claim 2, wherein the platinum metal is platinum.

4. A process as claimed in claim 3, wherein the catalyst consists of 1 to 10% by weight of platinum on a carrier.

5. A process as claimed in claim 4, wherein the carrier is active carbon.

6. A process as claimed in claim 1, wherein the oxidation is carried out at a pressure in the range from 0.5 to 100 bar.

7. A process as claimed in claim 6, wherein the oxidation is carried out at a pressure in the range of from atmospheric pressure to 10 bar.

8. A process as claimed in claim 7, wherein the oxidation is carried out at atmospheric pressure.

9. A process as claimed in claim 1, wherein the aqueous medium also contains a solubilizer inert towards the reactants under the reaction conditions.

10. A process as claimed in claim 9, wherein the solubilizer is present in an amount of from 10 to 75% by weight, referred to the amount of water and solubilizer.

11. A process as claimed in claim 10, wherein the solubilizer is present in an amount of from 30 to 50% by weight, referred to the amount of water and solubilizer.

12. A process as claimed in claim 9, wherein the solubilizer is a glycol ether having no free hydroxy groups.

13. A process as claimed in claim 12, wherein the glycol ether has the formula $R^1O[CH_2CH(CH_3)O]_nR^2$, wherein n is an integer from 1 to 4 and $R^1$ and $R^2$ are equal or different alkyl groups having from 1 to 4 carbon atoms.

14. A process as claimed in claim 13, wherein the solubilizer is diethyleneglycol dimethylether.

15. A process as claimed in claim 1, wherein the oxidation is carried out at a temperature in the range of from 30° C. to the boiling point of the aqueous medium.

16. A process as claimed in claim 15, wherein the oxidation is carried out at a temperature in the range of from 50° to 95° C.

17. A process as claimed in claim 15, wherein the oxidation is carried out at a temperature in the range of from 60° to 90° C.

18. A process as claimed in claim 1, wherein the aqueous medium contains, at the beginning of the oxidation, 5 to 30% by weight of 5-hydroxymethylfurfural, referred to the amount of aqueous medium.

19. A process as claimed in claim 1, wherein the pH-value is adjusted to a range of from 6.5 to 8 during the oxidation by the addition of a base.

20. A process as claimed in claim 19, wherein the pH-value is adjusted to a range of from 7 to 7.5 during the oxidation by the addition of a base.

21. A process as claimed in claim 1, wherein the oxidation is started at a pH-value of about 7 and is carried out without addition of an acid or a base.

22. A process for the oxidation of 5-hydroxymethylfurfural which comprises oxidizing at a pH of at most 8 5-hydroxymethylfurfural in an aqueous medium with oxygen in the presence of a catalyst which contains a metal of the platinum group, selected from the group consisting of platinum, palladium and a combination thereof on active carbon at a pressure in the range of from atmospheric pressure to 10 bar at a temperature in the range of from 50° C. to the boiling point of the aqueous medium, the aqueous medium containing from 5 to 30% by weight of 5-hydroxymethylfurfural, referred to the aqueous medium.

23. A process for the oxidation of 5-hydroxymethylfurfural which comprises oxidizing 5-hydroxymethylfurfural in an aqueous medium at a pH value of at most 8 with oxygen in the presence of a catalyst which contains at least one metal of the platinum group, the aqueous medium also containing a solubilizer inert towards the reactants under the reaction conditions in an amount of from 10 to 75% by weight, referred to the amount of water and solubilizer, the reaction being started at a pH value of about 7 and carried out without addition of an acid or a base and also carried out at a temperature in the range of from 50° C. to the boiling point of the aqueous medium.

* * * * *